(12) United States Patent
Mosharraf et al.

(10) Patent No.: US 11,559,577 B2
(45) Date of Patent: Jan. 24, 2023

(54) IMMUNOGENIC COMPOSITION FORMING A VACCINE, AND A METHOD FOR ITS MANUFACTURE

(71) Applicant: Engimata, Inc., Pleasanton, CA (US)

(72) Inventors: Mitra Mosharraf, Danville, CA (US); Aryo Sorayya, Danville, CA (US); Rajiv Nayar, Danville, CA (US)

(73) Assignee: Engimata, Inc., Pleasanton, CA (US)

( * ) Notice: Subject to any disclaimer, the term of this patent is extended or adjusted under 35 U.S.C. 154(b) by 28 days.

(21) Appl. No.: 17/204,511

(22) Filed: Mar. 17, 2021

(65) Prior Publication Data

US 2021/0299244 A1 Sep. 30, 2021

Related U.S. Application Data

(63) Continuation-in-part of application No. 16/925,438, filed on Jul. 10, 2020, now Pat. No. 11,278,617.

(60) Provisional application No. 63/003,254, filed on Mar. 31, 2020.

(51) Int. Cl.
| | |
|---|---|
| *A61K 39/215* | (2006.01) |
| *B82Y 5/00* | (2011.01) |
| *A61K 47/69* | (2017.01) |
| *A61K 39/00* | (2006.01) |

(52) U.S. Cl.
CPC ........ *A61K 39/215* (2013.01); *A61K 47/6911* (2017.08); *A61K 2039/53* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 9,603,799 B2 * | 3/2017 | Sorayya | A61K 9/0019 |
| 10,494,406 B2 | 12/2019 | Sawada et al. | |
| 10,584,356 B2 | 3/2020 | Ter Meulen et al. | |
| 10,588,963 B2 | 3/2020 | Stegmann et al. | |
| 2012/0164181 A1 | 6/2012 | Moser et al. | |
| 2014/0341974 A1 | 11/2014 | Sorayya et al. | |
| 2017/0258893 A1 | 9/2017 | Weiner et al. | |
| 2019/0359990 A1 | 11/2019 | Tuller et al. | |
| 2020/0009244 A1 | 1/2020 | He et al. | |

OTHER PUBLICATIONS

He et al., Journal of Immunology, 2004, 173:4050-4057. (Year: 2004).*
He et al., Journal of Virology, 2006, 80(12):5757-5767. (Year: 2006).*
Restifo et al., Gene Therapy, 2000, 7:89-92. (Year: 2000).*
International Search Report; PCT/US21/41245; dated Dec. 30, 2021;By: Authorized Officer Kari Rodriquez.

* cited by examiner

*Primary Examiner* — Nicole Kinsey White
(74) *Attorney, Agent, or Firm* — Caldwell Intellectual Property Law

(57) ABSTRACT

An immunogenic composition forming a vaccine includes a nanoparticle delivery system comprising at least a nanoparticle, wherein the at least a nanoparticle comprises a lipid layer exterior including a plurality of lipids, cholesterol, and a primary alkyl amine including a positively charged amino group head and at least a carbon tail and an antigen incorporated in the at least a nanoparticle, wherein the antigen comprises a nucleic acid encoding a protein from a coronavirus.

21 Claims, 10 Drawing Sheets

IMMUNOGENIC COMPOSITION FORMING A VACCINE, AND A METHOD FOR ITS MANUFACTURE

CROSS-REFERENCE TO RELATED APPLICATIONS

This application is a continuation-in-part of U.S. Provisional patent application Ser. No. 16/925,438, filed on Jul. 10, 2020 and entitled "IMMUNOGENIC COMPOSITION FORMING A VACCINE, AND A METHOD FOR ITS MANUFACTURE," which claims the benefit of priority of U.S. Provisional Patent Application Ser. No. 63/003,254, filed on Mar. 31, 2020 and entitled "LIPOSOMAL VACCINE ADJUVANT FOR VIRUS SPIKE PROTEINS AND METHODS OF MAKING AND USING SAME." The entirety of U.S. Provisional patent application Ser. No. 16/925,438 and U.S. Provisional Patent Application Ser. No. 63/003,254 is incorporated herein by reference.

FIELD OF THE INVENTION

The present invention generally relates to the field of vaccine compositions and methods of making and using the same. In particular, the present invention is directed to an immunogenic composition forming a vaccine, and a method for its manufacture.

BACKGROUND

Coronaviruses are an emerging pandemic threat that humans rarely have innate immunity to. Infection typically results in mild respiratory symptoms but can be more serious in infants and older adults, especially those with underlying comorbidities. Respiratory infection is second only to malaria as a cause of infant mortality worldwide and accounts for substantial hospitalization burden in both age groups in developed countries. Moreover, some pathogens, such as newly emergent zoonotic viral strains, can pose a significant risk of mortality to the general population as well.

SUMMARY OF THE DISCLOSURE

In an aspect, an immunogenic composition forming a vaccine includes a nanoparticle delivery system comprising at least a nanoparticle, wherein the at least a nanoparticle comprises a lipid layer exterior including a plurality of lipids, cholesterol, and a primary alkyl amine including a positively charged amino group head and at least a carbon tail and an antigen incorporated in the at least a nanoparticle, wherein the antigen includes a nucleic acid which encodes an antigenic protein.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1B:
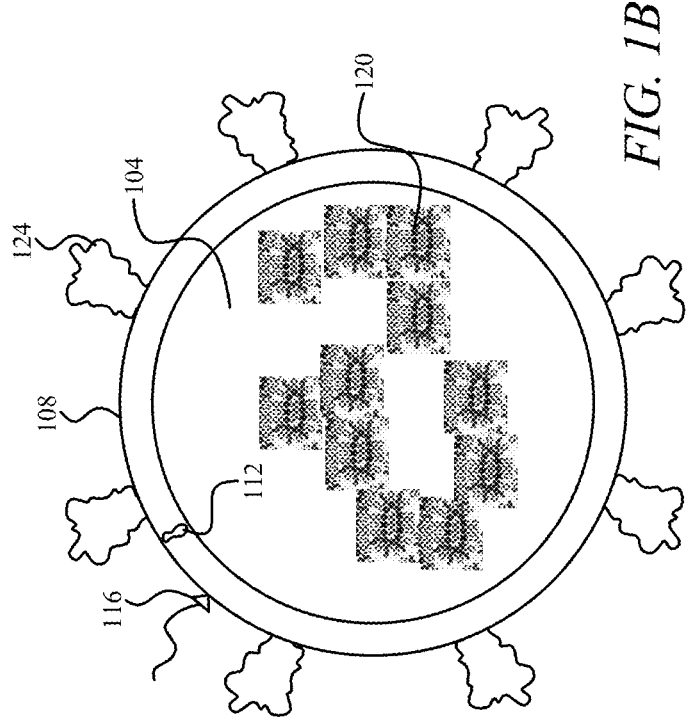
FIGS. 1A-B is a schematic diagram of an exemplary embodiment of an immunogenic composition.

Embodiments disclosed herein present a novel vaccine designed against spike proteins from coronaviruses, such as SARS-CoV-2, using a lipid-based nanoparticle nucleic acid formulation. Formulation may include a liposomal formulation. A resulting vaccine may be scalable, flexible in its antigen presentation, and have the potential for stability outside the cold chain. In an embodiment, a vaccine may include a positively charged chemical vaccine additive for cell targeting, and may include a liposomal vaccine delivery system with entrapped, embedded, and/or surface adsorbed nucleic acids encoding viral spike proteins and protein complexes of a variety of viruses belonging to the Coronaviridae family of viruses for efficient presentation of the viral spike proteins to the immune system. This presentation of the viral spike protein antigen may induce a strong immune response in vivo and lead to the generation of coronavirus-neutralizing antibodies and significant amelioration of infection to coronaviral infections.

Embodiments may include, as a non-limiting example, a liposomal or other lipid-based nanoparticle vaccine formulation that includes entrapped, embedded, and/or surface adsorbed nucleic acids, which may encode a variety of viral proteins, such as the surface exposed glycoproteins (spike proteins) of the SARS-CoV-2 virus, S1 and/or S2. These nucleic acids may encode forms of S1, S2, and/or combinations therein (such as a polycistronic form relating to the native genomic mRNA sequence, and/or a fused form where the separate proteins are encoded as a single polypeptide), which may adopt various oligomeric states, found on enveloped viruses such as coronaviruses. "Spike proteins" are glycoproteins responsible for binding to host cell surface receptors and subsequent viral entry and represent a preeminent source of potential antibody-recognizing antigens. These spike protein complexes are believed to elicit a protective adaptive immune response in generating neutralizing antibodies against the viral surface, resulting in antibody opsonization and prevention of viral-mediated entry into host cells via spike protein interactions with host cell receptors. A potential avenue to combat such viruses may thus be to create a vaccine against these spike proteins, and other similar glycoproteins, which have been extensively characterized for other human coronavirus such as SARS and MERS, as well as non-human animal coronaviruses such as PEDV, FPIV, and MHV. Presentation of these antigenic glycoproteins in a more physiologically relevant, lipid-associated presentation to the immune cells may be essential to eliciting an appropriate immune response.

The pandemic caused by the Severe Acute Respiratory Syndrome Coronavirus 2 (SARS-CoV-2), previously known as the 2019 novel coronavirus (2019-nCoV) is an example of such an enveloped virus that has a trimeric spike (S) protein at its viral surface. The trimeric S protein of SARS-CoV-2, consisting of an S1 protein and a S2 protein, is responsible for binding to the host cell surface receptor, angiotensin-converting enzyme 2 (ACE2), and trigger subsequent receptor-mediated viral entry into the host cell. Symptoms in infected patients include fever, coughing, malaise, night sweats, headache, and breathing difficulties that may ultimately be fatal, especially in elderly patients or those with underlying diseases. Additionally, there are human and non-human coronaviruses with significant health and/or economic impact or potential impact including, without limitation, SARS (Severe Acute Respiratory Syndrome), MERS (Middle Eastern Respiratory Syndrome), MHV (Mouse Hepatitis Virus), PEDV (Porcine Epidemic Diarrheal Virus), and FIPV (Feline Infectious Peritonitis Virus); the last three infect only non-human animals, but boast high mortality rates and rates of infection and attack economically and scientifically important species.

Figure 1A:
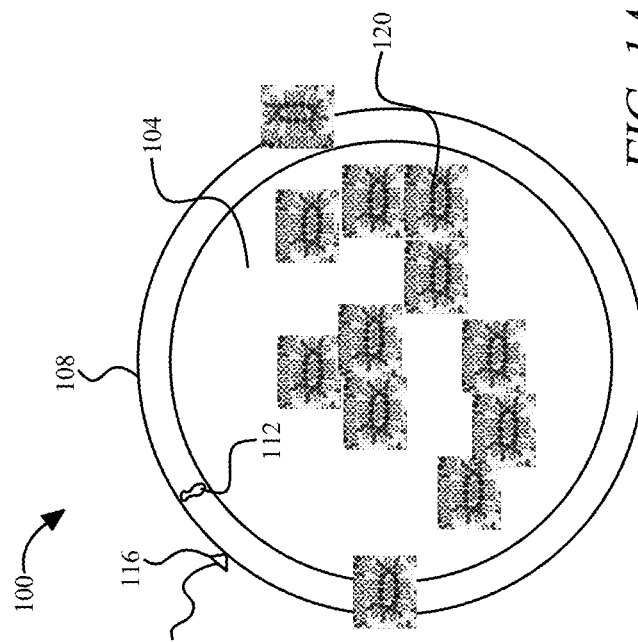

Referring now to FIG. 1A, an exemplary embodiment of an immunogenic composition 100 is illustrated. Immunogenic composition 100 includes a nanoparticle delivery system. A "delivery system," as used in this disclosure, is an object or plurality of objects used to deliver an antigen, as defined below, to a-location within living tissue, a living organism such as a human, or the like; the intended location may include, for instance, one or more immune cells, one or more locations within the one or more immune cells, one or more cells that may act as a host for protein transcription, or any other location that may occur to a person skilled in the art upon reviewing the entirety of this disclosure. A delivery system may include, in a non-limiting example, an adjuvant. An "adjuvant," as used in this disclosure, is a pharmacological and/or immunological agent that improves, or helps to stimulate, an immune response of a vaccine, antigen, or other immunologically active compound. Nanoparticle delivery system includes at least a nanoparticle 104. A "nanoparticle," as used in this disclosure, is a particle of matter between 1 and 2000 nanometers in diameter. For instance, and without limitation, at least a nanoparticle 104 may be engineered to have an average size less than 500 nm in diameter. At least a nanoparticle 104 may be engineered to have a diameter between 50 nanometers and 2000 nanometers. At least a nanoparticle may have a diameter between 50 nanometers and 1000 nanometers. At least a nanoparticle may have an average diameter of approximately 200-300 nanometers. At least a nanoparticle may include a plurality of particles, a large majority of which are between 80 nanometers and 500 nanometers in diameter; a small number of outliers may be between 5 nanometers and 1200 nanometers. At least a nanoparticle 104 may include a plurality of nanoparticles, which may be suspended, without limitation, in an aqueous medium, lyophilized, and/or cryogenically preserved as described in further detail below. At least a nanoparticle 104 includes a lipid layer 108 exterior including a plurality of lipids, which may vary in physicochemical properties. Lipid layer 108 exterior may include, without limitation, a lipid monolayer, bilayer, and/or multi-lamellar construction and/or lipid corona about a non-liposome nanoparticle, which may include any nanoparticle as described above, or the like. At least a nanoparticle 104 may include, for instance, a liposome. A "liposome," as used in this disclosure, is a vesicle enclosed by a lipid and/or phospholipid bilayer. Alternatively or additionally, at least a nanoparticle 104 may include a micelle, defined as a lipid monolayer enclosure, a micelle, an amphipol, a nanodisc, a styrene-maleic acid lipid particle (SMALP), and/or a nanostructure such as a piece of inorganic and/or organic material such as metal-based, metal oxide, carbon-based, immune-stimulating complex (ISCOM), protein cages, or other nanoparticles with a lipid material, or the like. Lipid and/or lipids making up lipid layer 108 and/or nanoparticle 104 construction may include, without limitation, phospholipids such as dipalmitoyl phosphatidylcholine (DPPC), dioleoyl phosphatidylcholine (DOPC), non-phospholipid lipids incorporating and/or combined with polyethylene glycols (PEGs), such as without limitation, PEGylated lipids, PEG-conjugated lipids, or the like, zwitterionic, neutral, cationic, and/or anionic phospholipids and non-phospholipids such as phosphatidylcholine, ceramides, phosphatidylethanolamine, saturated, monounsaturated and/or polyunsaturated fatty acid lipids, and the like. Lipids may be selected from the FDA GRAS list for approved excipients, for instance to guard against any biosafety issues. Lipid layer 108 includes cholesterol 112 and/or cholesterol 112 derivatives, including cholesterol with other functional groups added on; cholesterol derivatives may include, without limitation, cholesterol derivatives denoted as disterol-phospholipid Bis-Azo-PC, Chol-T, Chol-Q, or the like. Lipid layer 108 includes a primary alkyl amine 116, defined as a structure having an amine functional group and one or more carbon tails in an unbranched and/or branched carbon chains formation; primary alkyl amine 116 may include without limitation nonadecanamine, stearylamine, heptadecylamine, cetylamine, tripentylamine, and/or isomers of the alkyl amines, or the like.

Continuing in reference to FIG. 1A, primary alkyl amine 116 includes a positively charged amino group head and at least a carbon tail. Non-limiting examples of primary alkyl amine 116 include stearylamine (SA), pentylamine ($C_5H_{13}N$), alkyl amines of any carbon length, as well as branched alkyl amines such as tripentylamine, amylamines, or the like, mixtures of isomers of the above, and/or alkyl amines with varying degrees of poly- and mono-unsaturated carbon chains, such as alkene and/or alkyne substituted alkyl amines. Primary alkyl amine 116 may be positively charged. As a result, lipid layer 108 and/or at least a nanoparticle 104 may be positively charged; in an embodiment, positive charge of primary alkyl amine 116 may neutralize a net negative charge of at least a nanoparticle 104 and/or may cause overall charge of at least a nanoparticle 104 to become positive. In an embodiment, and without limitation, where at least a nanoparticle 104 is positively charged, at least a nanoparticle 104 may attract spike proteins having negative charges, improving entrapment and/or adsorption to lipid surface of spike protein. In a non-limiting example, a positive charge of combined nanoparticle and antigen may further have an effect of attraction to negatively charged cell membranes of immune and/or somatic cells, which may cause combined nanoparticle and antigen to contact and/or deliver into such cells the antigens; this may increase immunogenic effect of the resulting vaccine by improving cell-targeting. In some embodiments, spike proteins may alternatively or additionally complex bind to lipid layer; for in instance, spike protein may interact and change protein conformation to affect a complex bind, which may occur as a non-limiting example where a formulated vaccine is lyophilized and then reconstituted. In some embodiments, where antigen has a positive charge, alkyl amine and/or an additional compound having a negative charge, such as without limitation DPPG (dipalmitoyl, dioleoyl, disterylphosphatidylglycerol), alginate, and/or polyalginate, may be used to give lipid layer a net negative charge. Generally, where antigen has an electric charge with a first polarity, lipid layer exterior may have an electric charge with a second polarity, wherein the first polarity differs from the second polarity; i.e. a where the first polarity is negative the second polarity may be positive, and vice-versa.

Still referring to FIG. 1A, as a non-limiting example, materials used in lipid layer 108 and/or liposome may include cholesterol 112 at approximately 20 mol %, saturated lipids DPPC in an amount of approximately 20-40 mol %, SA, positively charged, at approximately 15-45 mol %, and unsaturated lipid DOPC neutral, at approximately 15-25 mol %. In a non-limiting, illustrative embodiment, ratios of lipids may be in a range of DPPC:DOPC:cholesterol 112: alkyl amine molar ratio is 20-40:15-30:20:10-45. In an embodiment, differing molar ratios may be used to optimize various recombinant forms of spike proteins, and/or improve adsorption of coronavirus spike proteins from other species.

Further referring to FIG. 1A, immunogenic composition 100 includes an antigen incorporated in the at least a nanoparticle 104. An "antigen," as used in this disclosure, is a viral molecule and/or molecular structure that may induce an antigen-specific antibody response and/or result in immune cell antigen receptor-binding that may be encoded in a nucleic acid sequence. Antigen, as used to herein, may refer to an antigenic protein and/or a nucleic acid encoding for an antigenic protein, a portion of an antigenic protein, a portion and/or entirety of a protein complex, or the like; more generally, nucleic acid may encode any protein, portion of protein, and/or chain of one or more amino acids. A "nucleic acid," as used in this disclosure, is a biomolecule consisting of at least a nucleotide. Nucleic acid 120 may include DNA and/or RNA macromolecules, which may be present as single-stranded (ss), double stranded (ds), circular, linear, supercoiled, relaxed, nicked, or in any other form nucleic acids may adopt to be packed and/or arranged in immunogenic compositions. Nucleic acid 120 may include any type of nucleic acid such as antisense oligonucleotide, small interfering RNA (siRNA), mRNA, plasmid DNA (pDNA), and the like. Nucleic acid may elicit an immune response, without limitation, by being transcribed into one or more proteins, such as spike proteins or the like as described in this disclosure.

Continuing in reference to FIG. 1A, nucleic acid may encode an S2 protein. Alternatively or additionally, nucleic acid may encode an S1 protein. In non-limiting exemplary embodiments, nucleic acid 120 may include positive sense (+)RNA molecules which may be translated directly into a polypeptide once entered into a cell, such as mRNA. Such nucleic acid 120 may mimic coronavirus genomic RNA as positive sense (+)RNA, which may be directly translated into a polypeptide in the cellular cytosol after internalization. In this way, the mRNA molecule is translated into at least a copy of the viral protein and then subsequently degraded, after some time, in the cytosol of the cell. Thus, the antigen is a biomolecular precursor, which is used as an mRNA template for ribosomal translation into viral-mimicking peptides. The nucleic acid acts as a pharmacologically active synthetic drug which is converted into protein after internalization into a cell.

In an embodiment, combination of antigen such as nucleic acid with a delivery mechanism as described in this disclosure may obviate any need to use solvents such as ethanol in generating a composition. Combination of positively charged lipids with negatively charged nucleotides such as RNA, and/or reconstituting solution of one or other with the other one, may enable composition without use of solvents during mixture and/or reconstitution, for instance as described below.

Referring now to FIG. 1B, in an embodiment, antigen may also include a spike protein from a coronavirus, which may include any virus in the subfamily Orthocoronavirinae. A "spike protein," as used in this description, is a protein and/or glycoprotein structure that projects from, lies, on, and/or traverses a surface of a virus particle. A spike protein in a coronavirus may be referred to as an "S" protein, for instance S1 or S2. Spike protein 124 may include without limitation a trimeric protein complex or one or more sub-units thereof, such as an S1 subunit, an S2 subunit, or the like, or homo- and/or hetero-oligomeric forms of these proteins. In an embodiment, and as described in further detail below, an S2 subunit may be embedded in a lipid bilayer of a virus particle, while a corresponding S1 subunit may bind to the S2 protein and project beyond the bilayer, extending away from the virus particle surface to engage host cells; this may enable a coronavirus to penetrate such cells by binding, for instance, the human ACE2 receptor, leading to internalization of the virus particle and/or a payload thereof, and ultimately infection. Spike protein 124, and/or any sub-unit thereof as described above may contain at least a post-translational modification (PTM) such as glycosylation, phosphorylation, acetylation, ubiquitination, isoprenoid attachment, or the like. Spike protein 124 may be recombinant, and/or may be harvested from partial and/or whole viral particles. For instance, and without limitation, spike protein may include NCP-CoV (2019-nCoV) spike protein (S1+S2 ECD) and/or SARS-CoV-2 (2019-n-Cov) Spike S1-His recombinant protein. Spike protein 124 may include a His tag; in such an example, a 'His tag' may be a poly-histidine amino acid fusion tag, as part of a recombinant spike protein, used for purification of the recombinant spike protein. Recombinant spike protein forms may contain purification tags, artifacts, or the like, including histidine tags, maltose-binding protein (MBP) tags, streptavidin-biotin tags, FLAG tags, and the like. Recombinant spike proteins and/or any viral glycoproteins used in nanoparticle formulations may originate from prokaryotic and/or eukaryotic recombinant expression systems, for instance and without limitation, mammalian cell expression, bacterial cells expression, yeast cell expression, and insect cell-baculoviral expression systems, and the like. Recombinant spike proteins and/or viral glycoproteins may be modified in DNA sequence to optimize recombinant expression and/or purification, but still result in faithfully recapitulated amino acid sequences resembling native viral proteins. Spike protein 124 may be HPLC-verified. Persons skilled in the art, after reviewing the disclosure in its entirety, will be aware of the various forms purified recombinant viral proteins may present.

With continued reference to FIG. 1B, a spike protein 124 or other antigen may include, without limitation, a glycoprotein. A glycoprotein is a surface-exposed viral structural protein that contains glycans-carbohydrate PTMs on the surface and/or within the protein. An S1 glycoprotein of a coronavirus may be, without limitation a homotrimer, a monomer, and/or a dimer. A process whereby glycans are chemically modified onto a surface of a glycoprotein is referred to as the process of "glycosylation," and is a post-translational modification (PTM) defined as a chemical attachment to a protein after synthesis in the cell. Glycosylation may function to shield, or otherwise alter, antigenic sites on a virus for immune cell avoidance. Different glycosylation states may exist for glycoproteins such as SARS-CoV-2 glycoproteins, including without limitation other PTMs such as hydroxylation, methylation, lipidation, acetylation, disulfide bond formation, ubiquitination, SUMOylation, phosphorylation, proteolysis, and the like, as described above. Depending on the recombinant source, there may be final glycosylation states that differ in their modification pattern, amount, branching, and physicochemical properties, and potentially their immunogenicity; for instance, different forms of glycosylation may result from recombinant production of spike proteins in insect, mammalian, bacterial, and yeast cells or other organisms used for recombinant manufacture of the spike protein. In some embodiments, spike proteins used may evince varying truncated and/or mutated forms such as forms having various amino acid mutations.

Further referring to FIG. 1B, in alternative embodiments, antigen may include one or more surface proteins of other types of viruses, such as without limitation influenza virus or respiratory syncytial virus (RSV). Antigen may alternatively or additionally include surface proteins besides spike proteins, such as "M" proteins; in an embodiment, use of a mixture of S proteins and M proteins may modify and/or improve overall immunogenicity, stability, glycoprotein packing, or the like.

Continuing in reference to FIG. 1B, it is important to note that liposome-based immunogenic composition 100 for generating adaptive immune response in humans from, for instance SARS-CoV-2, may incorporate combinations of nucleic acid 120 payloads and Liposome-incorporated spike protein 124. In this way, the formulation may provide spike proteins directly for antigen processing, as well as a template nucleic acid for generating additional antigens. This may represent a strategy for increasing 1) the immunological kinetics where there is a short burst of viral antigens present followed by a slower development of viral antigens as the mRNA is being translated. The immunological kinetics allow for Toll-Like Receptors (TLRs) and/or MI-IC Receptors to generate stable interactions with the viral proteins initially provided. Secondarily, additional viral peptides may be translated after the first "batch" of viral proteins is processed. And 2) potentially allow for multi-epitopes. Viral proteins translated from mRNA may have the benefit of multi-directionality where all surfaces are outwardly exposed for recognition. The polarity of the viral protein may not necessarily be maintained, where there is no lipid-embedded side and solvent-accessible side.

Continuing in reference to FIG. 1B, mRNA may comprise a first half-life in the cell, and the spike protein a second half-life, wherein the half-lives differ enough to provide temporal differences in immunology kinetics. The mRNA may thus be degraded soon after being translated, whereas the spike protein may be processed much quicker and prior to translation of mRNA. This way each antigen may be present only as long as necessary under normal cellular conditions to prepare viral proteins for display to immune cells. Nanoparticle 104 immunogenic compositions may have the benefit of encapsulating nucleic acid 120 antigens which encode for viral components. Nucleic acid 120 may include mRNA sequences for coronavirus spike protein 124 S1 and/or S1S2, as described herein. In such an instance, the nucleic acid 120 acts as an antigen precursor, which is translated into the de facto recombinant viral glycoprotein (surface antigen) which may then be recognized as the true antigen for which an adaptive immune response will be mounted.

Alternatively and/or additionally, and with continued reference to FIGS. 1A-B, nucleic acid 120 may be used in lieu of spike protein 124 for eliminating unnecessary antigenic load, potentially decreasing chances of allergic responses. For instance and without limitation, nucleic acid 120 may encode short immunogenic peptide fragments with the ability to elicit strong and targeted immune responses, avoiding the chances of allergenic reactions and/or secondary immunogenic effects. This way, the need for spike protein 124 may be circumvented and replaced with libraries of short peptides which are anticipated to generate strong immunogenic response without encoding for the fully functional spike protein 124.

Figure 3:
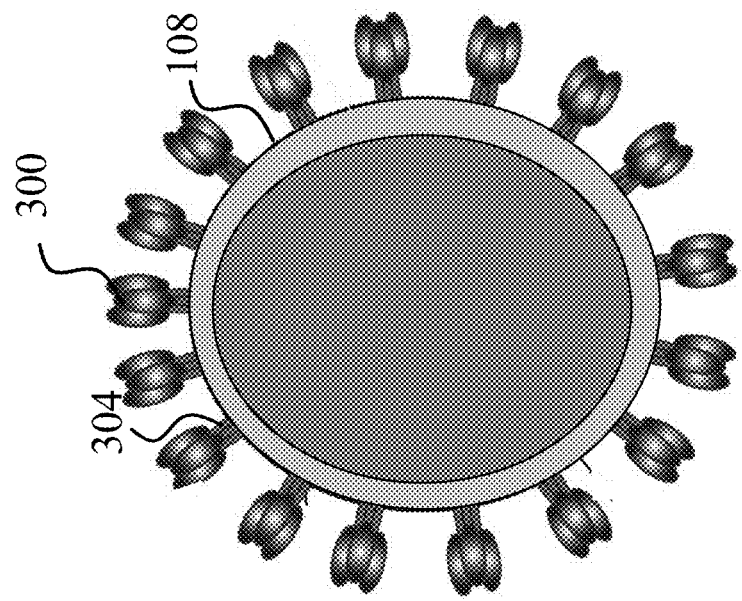
FIG. 3 is a schematic diagram of an exemplary embodiment of an immunogenic composition.
Figure 2:
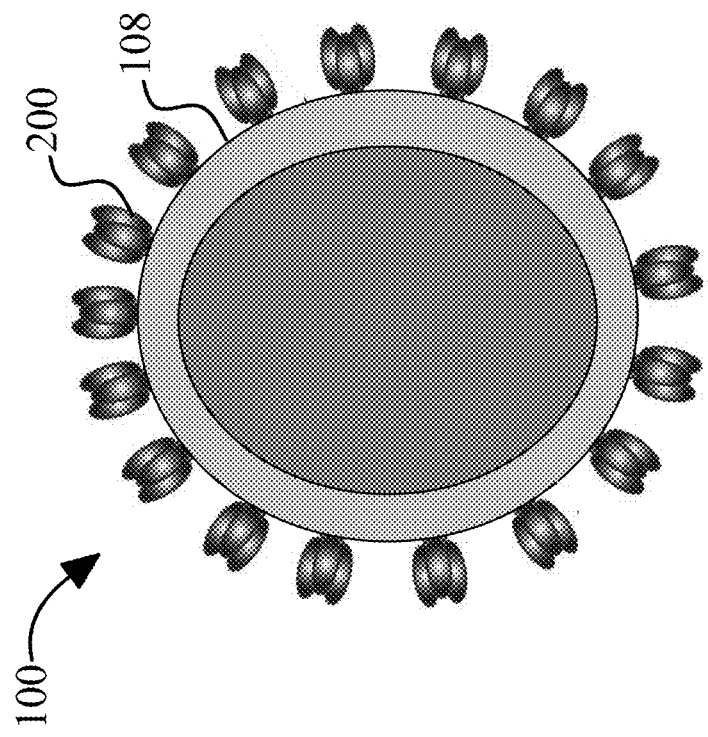
FIG. 2 is a schematic diagram of an exemplary embodiment of an immunogenic composition.
Figure 4:
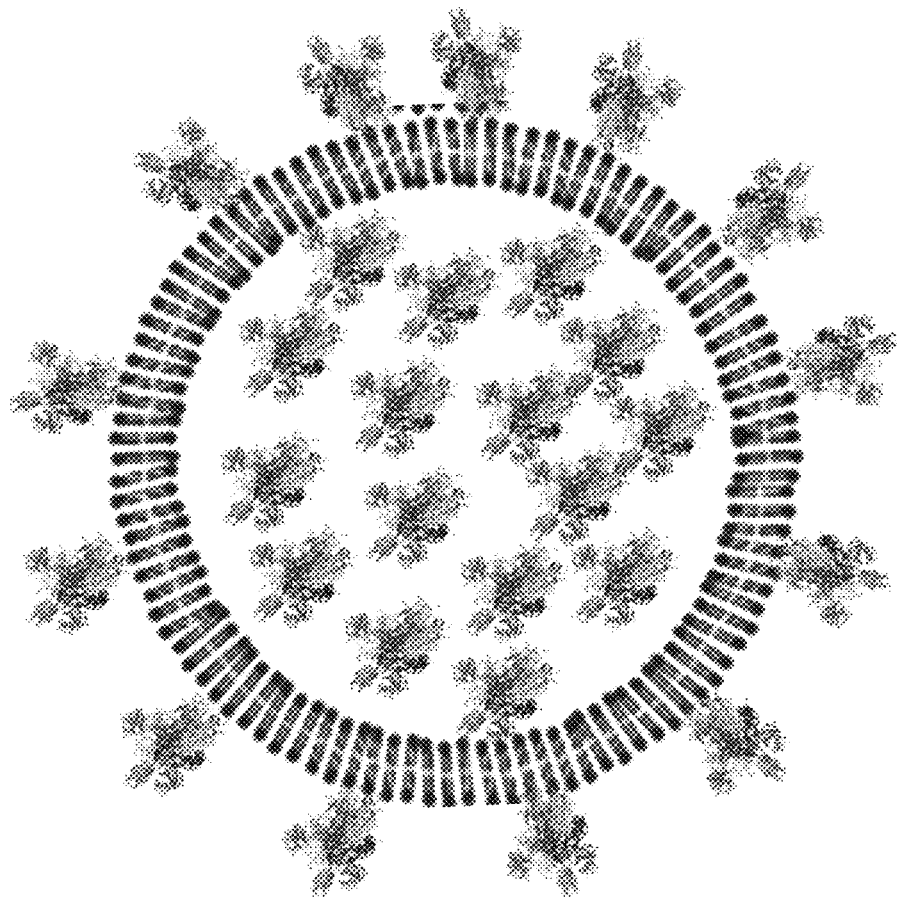
FIG. 4 is a schematic diagram of an exemplary embodiment of an immunogenic composition.

Referring now to FIG. 1B, antigen is incorporated in the at least a nanoparticle 104. "Incorporation," as used herein, is any form of attachment, adsorption, and/or entrapment on or in a nanoparticle; for instance, and without limitation, antigen may be adsorbed to a surface of lipid layer 108. As a non-limiting example, and as shown in FIG. 2, spike protein may include an S1 protein 200 without an S2 in complex with it, which may be attached to and/or adsorbed to lipid layer. As a further non-limiting example, and as illustrated in FIG. 3, spike protein may include an S2 protein 300 embedded in lipid layer 108, adsorbed to lipid layer 108 and/or bilayer, and/or interacting with lipid layer 108 and/or bilayer, and an S1 protein 304 projecting from the lipid layer 108. As a further non-limiting example, and as shown in FIG. 4, where nanoparticle includes or is a liposome, spike protein 124 may be entrapped in an aqueous compartment of the liposome, and/or may be adsorbed to lipid layer as well. Incorporation may include entrapment between layers of a bilayer; for instance, where lipid layer 108 includes a bilayer and/or multi-lamellar construction, spike protein may be entrapped within the bilayer.

Referring now to FIG. 1A, incorporation of nucleic acid 120 in nanoparticle 104 may include attachment and/or adsorption of nucleic acid 120 onto the surface of the nanoparticle 104. For instance and without limitation, such a nanoparticle 104 may use positively charged surface treatment, for instance with primary alkyl amine 116, such as stearylamine. Incorporation of nucleic acid 120 in nanoparticle 104 may include entrapment of nucleic acid 120 within the aqueous core of the nanoparticle 104. In an embodiment, combination of negatively charged nucleic acids such as RNA with positively charged lipids, liposomes, and/or nanoparticles may facilitate combination, entrapment, and/or attachment of the nucleic acids to, with, complexed with, and/or in the positively charged lipids, liposomes, and/or nanoparticles. This may be accomplished, in exemplary embodiments, without use of ethanol or other volatile solvents. A resulting combination may be positively charged, further attracting and/or being attracted to a negatively charged surface and/or target location. Alternatively or additionally, a resulting combination may be negatively charged, further attracting and/or being attracted to a positively charged surface and/or target location.

Continuing in reference to FIGS. 1A and 1B, in an embodiment, entrapment may improve nanoparticle 104 stability by housing nucleic acid 120 within an aqueous core. In an embodiment, nanoparticle 104 may have an aqueous and/or hydrophilic core; alternatively, nanoparticle may have many nested layers of lipids, between which antigen may be entrapped and/or with hydrophilic elements of which antigen may be combined and/or complexed. Although, it is anticipated that there may be stability issues with nucleic acid adsorbed onto the surface of a nanoparticle, such stability challenges may be found in the form of nucleases (freely circulating endo- and exonucleases), presence of reactive oxygen species, among other endogenous and exogenous reactive species, potential for degradation and modification with factors present within the blood, tissues, and the like. Alternatively or additionally, nucleic acid 120 may traverse the lipid bilayer 108 and/or be embedded within lipid bilayer 108. For instance, as depicted in FIGS. 1A and 1B, nucleic acid embedded within a unilamellar lipid structure where the polarity of some lipids solvating the nucleic acid are flipped such that ionizable groups may be in contact with the nucleic acid, and carbon chains outwardly facing. Nucleic acid 120 may be in complex with any lipid as described herein, including for instance ionizable aminolipids such as dilinoleylmethyl-4-dimethylaminobutyrate, DLin-MC3-DMA, and the like, "helper" lipids such as 1,2-distearoyl-sn-glycero-3-phosphocholine, DSPC, and the like, PEGs and/or PEGylated lipids such as 1,2-dimyristoyl-sn-glycerol, methoxypolyethylene glycol, PEG-DMG, among others, and/or cholesterol and/or cholesterol derivatives. Nanoparticle 104 for entrapment of nucleic acid 120 based immunogenic composition 100 may include nucleic acid particles solvated within a unilamellar lipid layer, among other lipid arrangements, within an aqueous core. Nanoparticle 100 may include viral glycoprotein and/or spike protein 124 antigen alone, nucleic acid 120 antigen alone, or combinations thereof. Nanoparticle 100 formulation may include nucleic acid 120 of multiple types of the same viral peptide. For instance and without limitation, nucleic acid 120 may include several mRNA transcripts for the pre-fusion glycoprotein, native glycoprotein, post-fusion form, individual small peptide sequences relating to various epitopes, among other forms. In further non-limiting illustrative examples, nucleic acid 120 may include mRNA corresponding to a plurality of different viral proteins, such that an immune response may be mounted against several different viral antigens. In either case, a more robust repertoire of epitopes for each antigen, or collection of antigens, may be used to cultivate a stronger, longer lasting adaptive immunological response. Nanoparticles 104 for nucleic acid 120 delivery may additionally differ in their lipid composition, surface properties, and size within the context of the physicochemical properties described herein. In an embodiment, combination of nanoparticles and antigens may be driven and/or enabled by ionic interaction due to opposite charges, for instance as described below, which may occur without limitation in hydrophilic portions of membrane or in core of a liposome, where nanoparticle includes a liposome. Antigen may complex with one or more parts of phospholipids, with one or more parts of lipids, and/or other elements of nanoparticle such as alkyl amine and/or stearylamine or other chemical components of nanoparticle.

With continued reference to FIGS. 1A and 1B, incorporation may be achieved by optimizing, or otherwise altering, the lipid composition, surface charge of the nanoparticle 104, and size of the nanoparticle 104, as well as other physicochemical properties. For example, an antigen such as an S1S2 spike protein of SARS-CoV-2 may be a negatively charged protein, for instance with acidic patches, that binds more efficiently to positively charged lipid surfaces and/or liposomes through favorable ionic interactions. Therefore, mixing a positively charged nanoparticle 104 such as a positively charged liposome with an S1S2 spike protein of SARS-CoV-2 may result in protein adsorption to the liposome and/or nanoparticle surface as well as some entrapment inside the liposome and/or nanoparticle. This particle-protein complex may subsequently interact with the immune cells and elicit a protective immune response in generating antibodies to the S1S2 spike protein. Such a protocol may be used for other antigenic proteins in generating a liposomal vaccine. Adsorption may be achieved, without limitation through ionic, hydrophobic, Van der Waals interactions, hydrogen bonding, and/or through covalent interactions and/or conjugation. Methods of manufacture as described in further detail below may entrap the target antigen inside a liposome as well as decorating the liposome surface with spike proteins by adsorption through molecular interactions. Where at least a nanoparticle 104 includes a liposome, liposome composition may be chemically modified to an appropriate surface charge that maximizes binding of target antigen to surface of the liposome and for presentation of the liposomes to the immune cells.

In an embodiment, and still referring to FIG. 1B, antigen may include a combination of above-described elements. For instance, and without limitation, antigen may include a nucleic acid and an antigenic protein; nucleic acid may encode antigenic protein and/or may encode a different protein. In an embodiment, at least a nano particle may be combined with nucleic acid and antigenic protein in distinct ways and/or in distinct manufacturing steps. For example, and without limitation, a first antigen element, which may be either nucleic acid or protein, may be combined first with at least a nanoparticle using first combination step as described in further detail below, such as reconstitution of lyophilized nanoparticle with the first element, which may lead to entrapment of first element within nanoparticle, and second with a second element, which may be any of nucleic acid and protein, for instance by addition of second element after reconstitution of nanoparticle solution; a result may be entrapment of first element within nanoparticle while second element may be complexed with, attached on, embedded in, and/or complexed with lipid surface.

Referring now to FIG. 4, immunogenic composition may be manufactured, stored, and/or prepared in one or more lyophilized forms and/or in one or more dried states using various drying technologies such as without limitation spray drying, vacuum drying, foam drying, or the like. For instance, and without limitation, immunogenic composition and/or one or more components thereof may be presented in an on-demand format in which composition is lyophilized for stability, then reconstituted for use. For instance, and without limitation, immunogenic composition may be formulated as a lyophilized composition, after incorporation of antigen in at least a nanoparticle 104. Alternatively or additionally, nanoparticle delivery system may be lyophilized separately and reconstituted with the antigen; in other words, incorporation may be performed concurrently with reconstitution. Reconstitution may refer to resuspension, hydration, solvation, or otherwise reconstituted in aqueous solution, including buffer compositions such as phosphate-buffered saline (PBS), or the like. In further non-limiting illustrative embodiments, reconstitution of a lyophilized nanoparticle, such as a liposome-glycoprotein complex, may be performed with varying salt concentrations, such as sodium chloride. In an embodiment, reconstitution of separately lyophilized nanoparticles with antigen may cause antigen to be trapped within a vesicle and/or other interior such as an aqueous interior of a liposome as well as attached to a surface thereof.

Still referring to FIG. 4, immunogenic composition 100 may include at least one lyoprotectant. A lyoprotectant, as used in this disclosure, is a substance that protects a substance during cryogenic freezing, during freeze-drying, and/or during freeze-thaw cycles. At least one lyoprotectant may include, without limitation, a polyol, such as without limitation sucrose, trehalose, mannitol, or the like, and/or at least one ionic strength balancing component, including for instance a salt, pH buffer, or the like. At least one lyoprotectant may include an amino acid, such as without limitation glycine, arginine, or the like. Persons skilled in the art, upon reviewing the entirety of this disclosure, will be aware of various alternative or additional lyoprotectants, cryoprotectants, and the like that may be employed consistently with this disclosure.

Still referring to FIG. 4, immunogenic composition 100 may include any suitable combination of elements including without limitation any set of formulations as set forth below in table 1. Formulations may include without limitation protectants such as sugar, pH control buffers, preservatives such as polysorbate 20%, and/or an ingredient such as NaCl or other salts to balance ionic strength.

TABLE 1

Exemplary Formulations

| Vaccine | S1 | S1-S2 | Lipid$^a$ | pH | Buffer | Polysorbate 20% | Sugar |
|---|---|---|---|---|---|---|---|
| B-S1 | 10 µg/mL | — | 25 mg/mL | 7.2 | Histidine | 0.05 | 10% Sucrose |
| B-S1S2 | — | 10 µg/mL | 25 mg/mL | 7.2 | Histidine | 0.05 | 10% Sucrose |

$^a$including cholesterol 112 and alkyl amine.

Still referring to FIG. 4, vaccine may be administered in any suitable manner. In an embodiment, vaccine may be injectable. Vaccine may alternatively or additionally be absorbed through a mucous membrane, for instance via aerosolized delivery to the nostrils and/or lungs. Alternatively or additionally, vaccine may be administered using a patch, such as without limitation a microneedle patch that delivers lyophilized vaccine in powder form; as a non-limiting example, lyophilized vaccine may be included in soluble microneedles which upon insertion to tissue of a living organism may dissolve in fluids thereof, reconstituting and activating the vaccine. As a further non-limiting example, lyophilized vaccine may be delivered in an implant such as a soluble or insoluble needle inserted under the skin or into other tissue allowing fluids of the subject tissue to reconstitute and disseminate the vaccine. Vaccine may be delivered in liquid and/or lyophilized form to any mucous membrane; for instance and without limitation, vaccine may be delivered as a lyophilized inhalable powder for absorption in nasal and/or pulmonary surfaces. Vaccine may be delivered orally, for instance in a needle or other device for injecting lyophilized vaccine into and/or across digestive tissues, which may be delivered in a capsule designed to disintegrate in one or more digestive juices. Vaccine in lyophilized form may be delivered by a nanobot.

Figure 5:
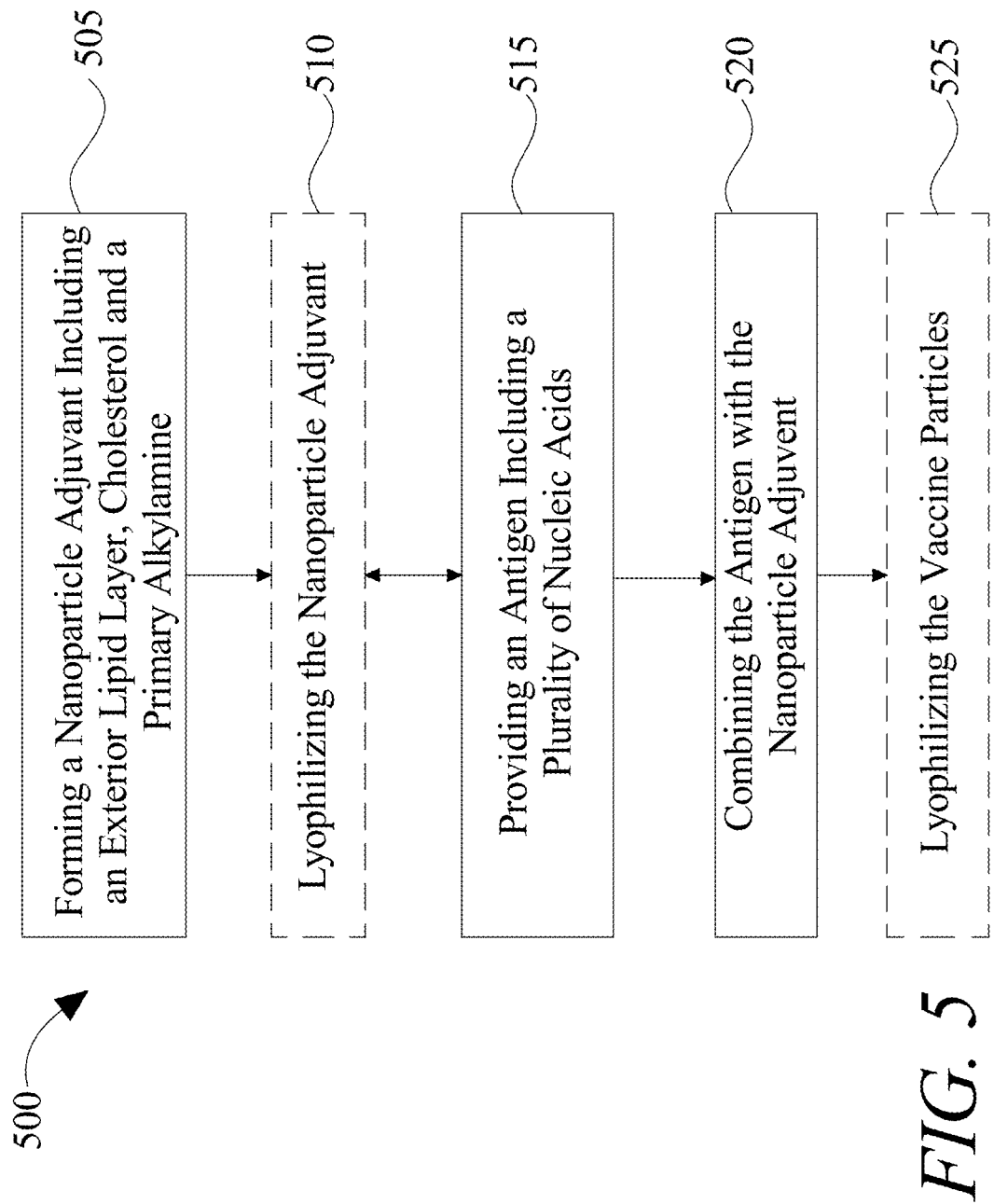
FIG. 5 is a flow diagram illustrating an exemplary embodiment of a method for manufacture of an immunogenic composition.

Referring now to FIG. 5, an exemplary embodiment of a method 500 of manufacturing an immunogenic composition forming a vaccine is illustrated. At step 505, a nanoparticle delivery system is formed. Nanoparticle delivery system may include any nanoparticle delivery system as described above. Nanoparticle delivery system includes a plurality of nanoparticles, which may include any nanoparticles as described above. Each nanoparticle includes a lipid layer 108 exterior including a plurality of lipids, cholesterol 112, and a primary alkyl amine 116 including a positively charged amino group head and at least a carbon tail, for instance and without limitation as described above. Lipid layer 108 may be positively charged, for instance by application of a concentration of a positively charged alkyl amine as described above. Each nanoparticle may include, without limitation, a liposome.

Still referring to FIG. 5, formation of nanoparticle delivery system may include formation of a suspension of liposomes. Formation may include hydrating a dried lipid blend, such as without limitation a freeze-dried lipid blend, and extruding the resulting solution through a filter having pore sizes at approximately an upper limit of a desired liposome diameter, which may be a desired diameter falling into ranges and/or average sizes as described above.

At optional step 510, combining may include lyophilizing the nanoparticle delivery system, for instance and without limitation as described in further detail below.

At step 515, and still referring to FIG. 5, method 500 includes providing an antigen. Antigen may include a plurality of nucleic acids encoding a plurality of peptides from a coronavirus, as described above. For instance, and without limitation, nucleic acid may include a sequence encoding an S1 protein. Nucleic acid may include a sequence encoding an S1S2 protein. Antigen added with nanoparticle may include nucleic acid alone and/or in combination with spike protein. Intact antigen and/or various specific domains, such as S1 and S2 subunits may be recombinant; for instance, and without limitation, intact antigen and/or specific domains and/or subunits may be manufactured using mammalian cell-culture based expression systems, or a plurality of expression systems as described above. Alternatively or additionally, whole and/or partial virus particles may be generated and/or replicated, and spike proteins and/or subunits may be extracted, separated from, sheared off, or otherwise purified from such whole or partial virus particles, or virus-like particles.

With continued reference to FIG. 5, antigen may encode for a spike protein including a glycoprotein. Glycosylation of spike protein may occur during production and/or replication of virus particles. Glycosylation of spike protein may include providing glycosylated spike protein in immunogenic composition and/or spike protein forms encoded in nucleic acid with specific glycosylation sites. Glycosylation may be varied across batches and/or populations of spike proteins, among individual spike proteins, and/or among the different cell types that translate nucleic acid; this may generate a recombinant glycoprotein library with glycoproteins of varying degrees of glycosylation. In an embodiment, spike proteins of varying glycosylation may be combined in the antigen; this may result in nanoparticles, such as liposomes, incorporating a plurality of different glycoproteins of the same species. In an embodiment, such liposomes may allow for greater immunogenicity. For instance, and without limitation, preparation of S1 may include reconstituting S1 in water for injection (WFI) to generate a given concentration, including without limitation a 250 µg/mL S1 stock solution. Specific amounts of S1 stock solution may then be diluted in specific amounts of a formulation buffer, which may include without limitation a 0.01% polysorbate 20/sucrose/histidine buffer to a concentration of approximately 10 µg/mL S1. As a further non-limiting example, a 550 µg/mL S1S2 stock solution, which may be reconstituted without limitation as described above, may be diluted in specific amount of formulation buffer, including any buffer as described above, to a concentration of approximately 10 µg/mL S1S2. Buffer may generally include any buffer offering a buffering capacity within a pH range of 6.0-7.5, including without limitation histidine and/or phosphate buffer. Buffer may include a polysorbate 20 or 80 concentration within a range of 0.001%-0.05%. Buffer may include a polysorbate 20 or 80 concentration within a range of 0.001%-0.05%.

At step 520, and still referring to FIG. 5, antigen is combined with nanoparticle delivery system. In an embodiment, a suspension of protein antigen may be added to an aqueous suspension of nanoparticle delivery system, using a mixing device to get a homogeneously distributed antigen-liposome mixture. Mixing device may include, without limitation, a magnetic stirrer, a sonication device, a homogenizer, or the like. Mixture may alternatively or additionally be swirled mechanically or manually. Combination according to this technique may tend to produce surface-mounted antigens and/or antigens adsorbed to lipid surface, for instance as described above. Combination according to this technique may tend to produce surface-attached antigen, antigen traversing lipid surface, and/or antigen encapsulated in lipid and/or aqueous core of lipid, for instance as described herein. Where nanoparticles have a charge with an opposite polarity to a charge of antigen, antigen may adsorb to the liposomes rapidly. In an embodiment, lyophilized nanoparticle delivery system may be reconstituted using a suspension of antigen in a buffer solution.

Alternatively or additionally, and continuing to refer to FIG. 5, hydration of lipid blend prior to extrusion may be performed with a solution and/or suspension of antigens; in other words, generation of nanoparticle delivery system may be performed concurrently with and/or subsequently to combination of antigen with nanoparticle delivery system. This may produce liposomes that include both entrapped and adsorbed antigens.

At step 525, and still referring to FIG. 5, vaccine particles formed according to any process as described above may be lyophilized. Lyophilized vaccine particles may be delivered and/or stored in lyophilized form and may subsequently be reconstituted prior to administration and/or may be administered in powdered and/or lyophilized form as described above.

Figure 6:
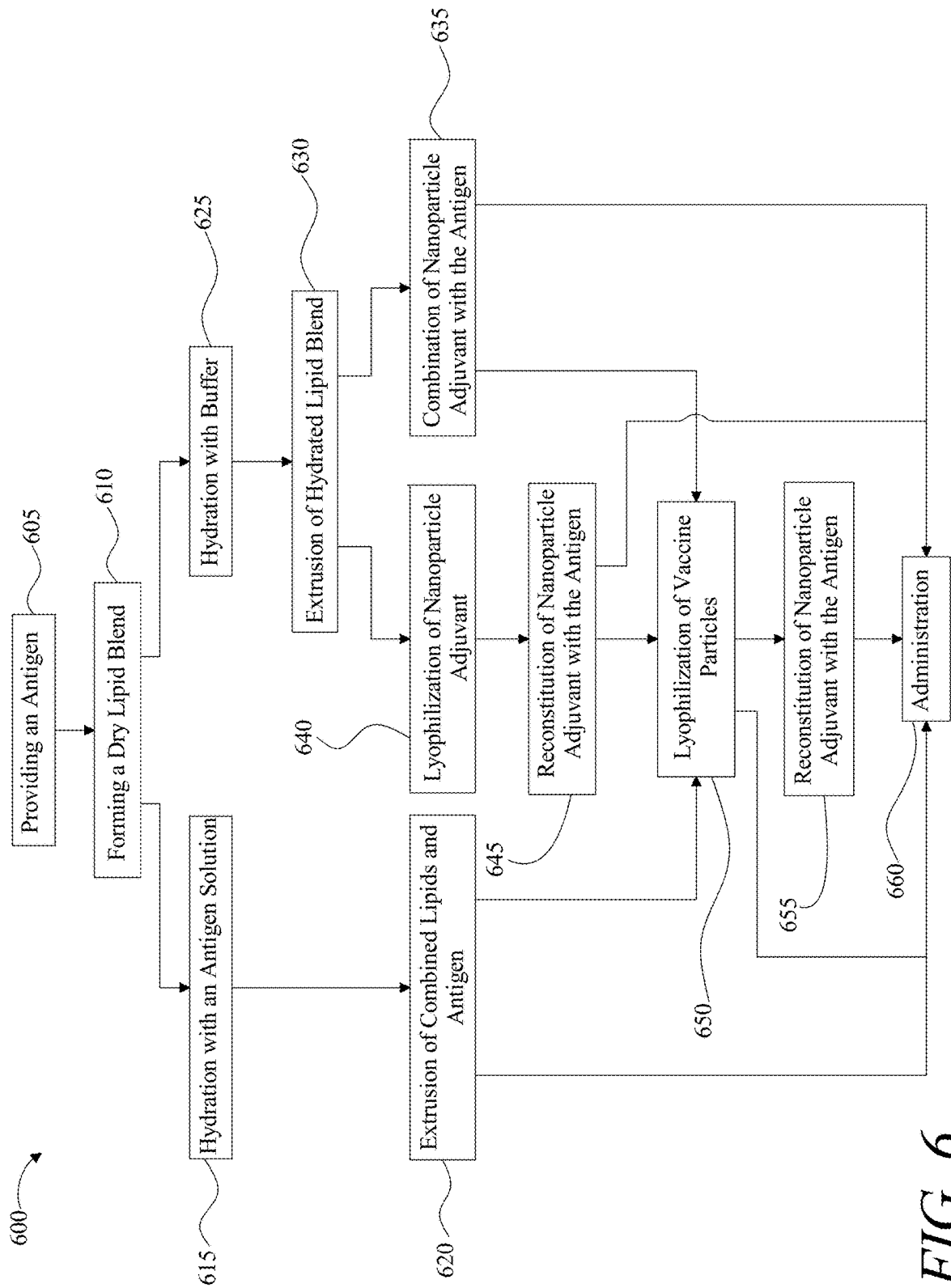
FIG. 6 is a flow diagram illustrating an exemplary embodiment of a method for manufacture of an immunogenic composition.
Figures 7, 8:
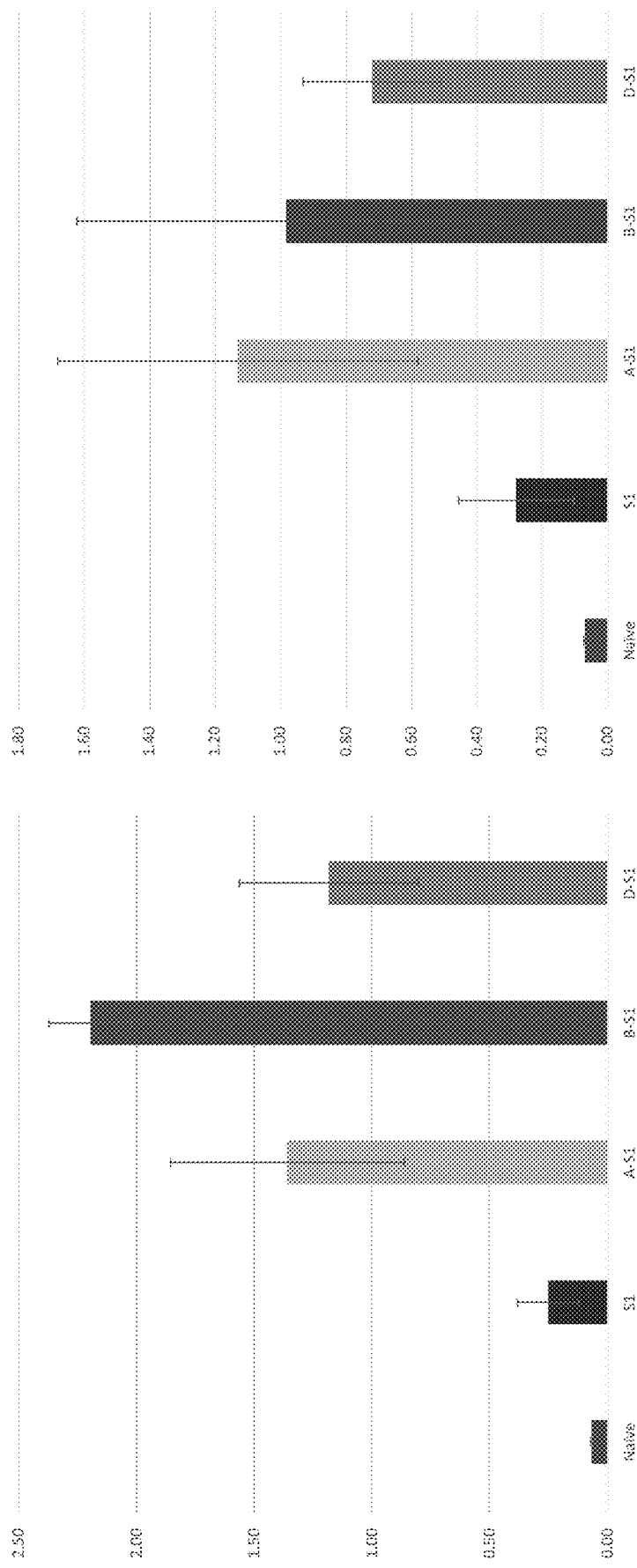
FIG. 7 is a bar graph illustrating experimental results describing relative immunogenicity.
FIG. 8 is a bar graph illustrating experimental results describing relative immunogenicity.
Figures 9, 10:
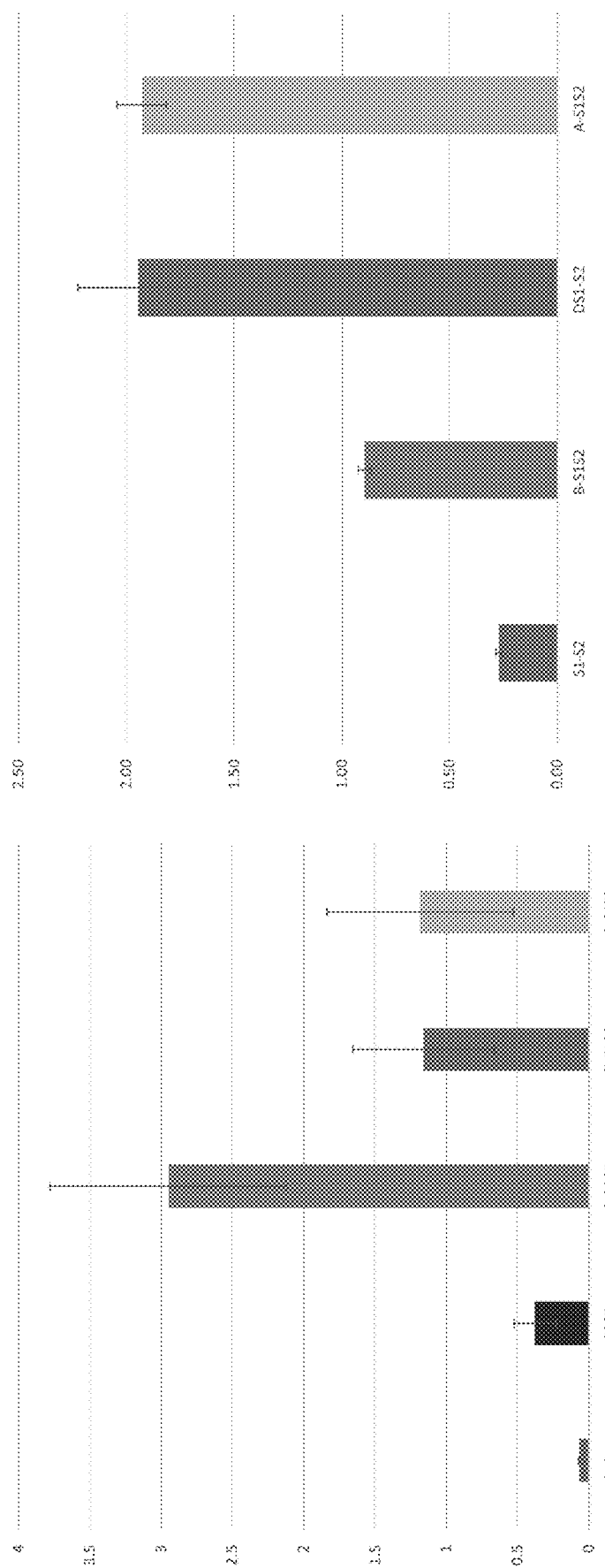
FIG. 9 is a bar graph illustrating experimental results describing relative immunogenicity.
FIG. 10 is a bar graph illustrating experimental results describing relative immunogenicity.
Figure 11:
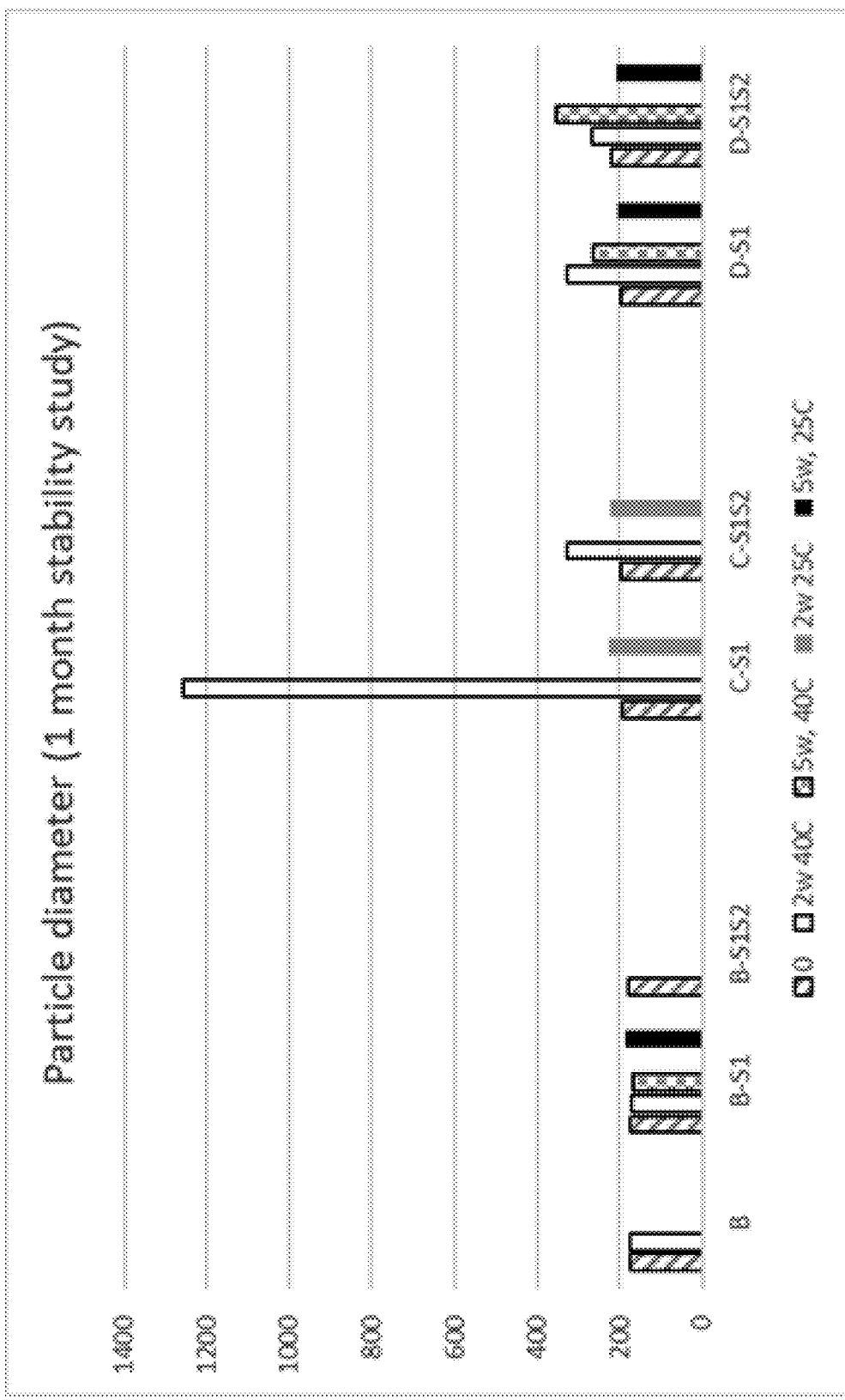
FIG. 11 is a bar graph illustrating experimental results describing stability over time.
Figure 12:
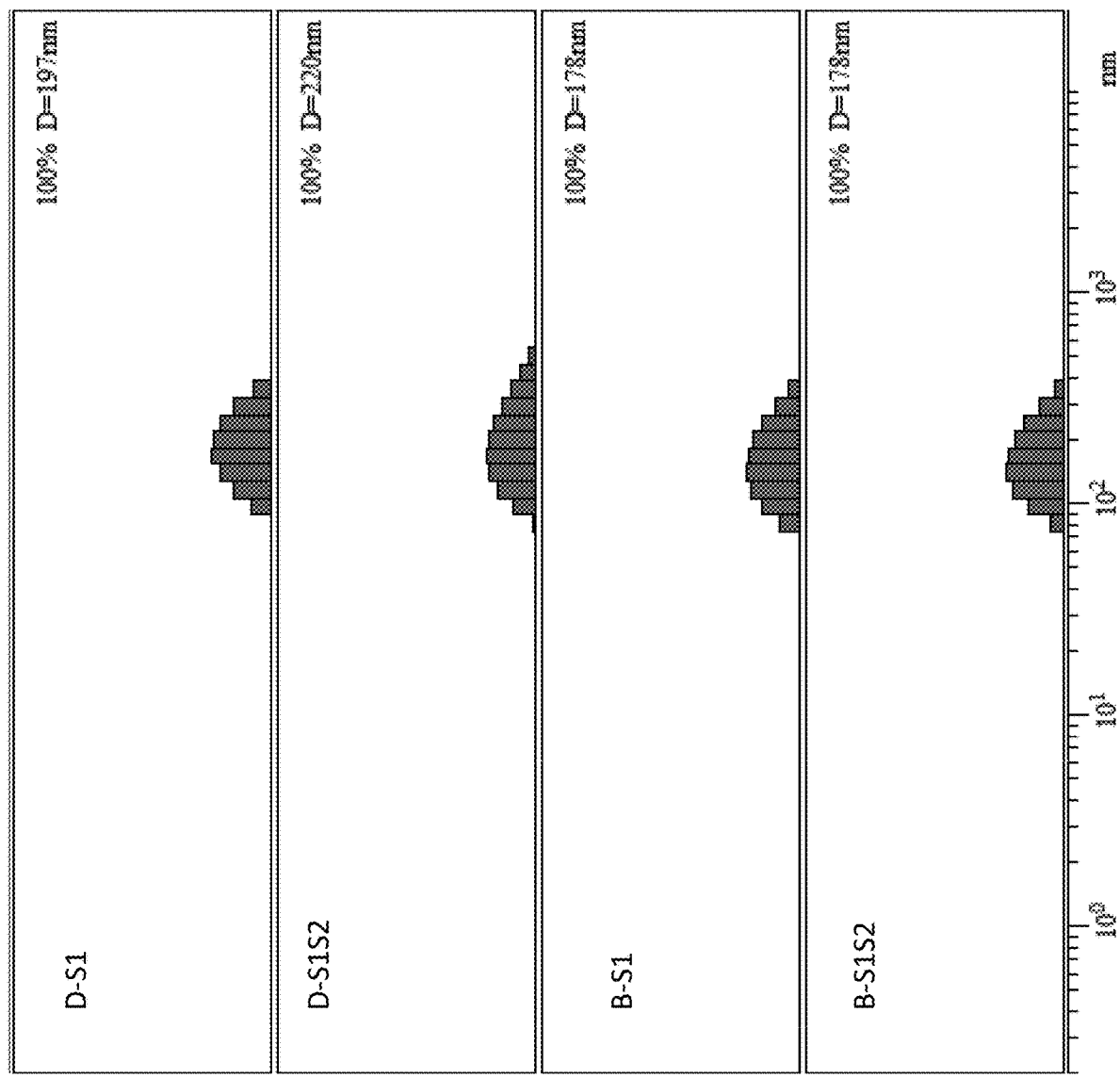
FIGS. 12 and 13 are histograms illustrating experimental results describing stability over time. The drawings are not necessarily to scale and may be illustrated by phantom lines, diagrammatic representations, and fragmentary views. In certain instances, details that are not necessary for an understanding of the embodiments or that render other details difficult to perceive may have been omitted.
Figure 13:
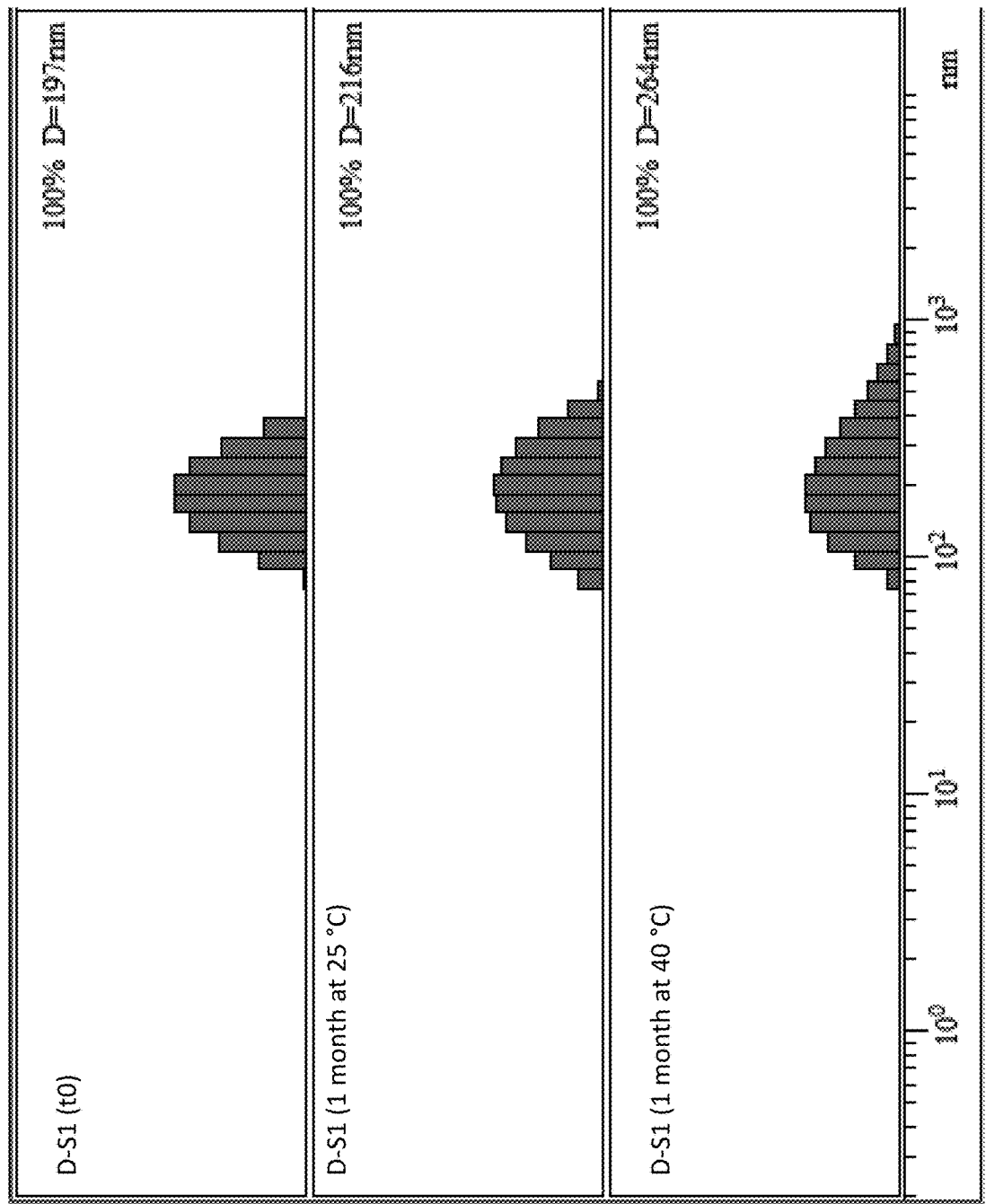

Referring now to FIG. 6, a flow diagram illustrating an exemplary embodiment of a method 600 of manufacturing an immunogenic composition forming a vaccine is illustrated. At step 605, an antigen is provided; antigen may include, without limitation, any antigen described above, including without limitation nucleic acid, spike proteins and/or glycoproteins of a coronavirus, and/or portions thereof. For instance, and without limitation, antigen may include nucleic acids encoding S1 glycoproteins and/or S1S2 glycoproteins. Provision of antigen may be performed, without limitation, according to any process described above in reference to FIGS. 1-5.

At step 610, and still referring to FIG. 6, a dry lipid blend may be provided and/or formed. As a non-limiting example, a blend of DPPC, DOPC, cholesterol and stearylamine (40:25:20:15:mol %, respectively may be dissolved in a chloroform/methanol/water solution. Solution may be dried, for instance in a rotary evaporator under a stream of nitrogen gas. Solution may subsequently be dissolved in a co-solvent of -cyclohexane/80% tertiary-Butyl alcohol (v/v) at a final lipid concentration of 20 mg/ml, for instance in aliquots of 50 mg of lipid/vial. Vials may then be lyophilized to obtain a dried lipid blend; vials may be sealed with nitrogen (N2) gas prior to partial placement of a stopper. Vials may then be freeze dried under a blanket of N2 gas, for instance in a freeze-dryer. As a non-limiting example lipid-blend may be lyophilized by freezing at −45° C., primary drying at −30 to −35 C, and secondary drying at 25-30° C. Freeze-dried lipid blend may be powdered; this may increase surface area compared to film deposited on a vial according to conventional methods. It has further been found that lyophilization of lipid blend and/or nanoparticles has produced unexpectedly strong immune responses compared to conventional combinations that do not involve lyophilization in intermediate states of manufacture.

Further referring to FIG. 6, lipid blend may be hydrated with an antigen solution and/or suspension, as illustrated at step 615. Antigen solution may include, without limitation antigen combined with a buffer to form a suspension. Buffer may include, without limitation, a lyoprotectant, which may include any lyoprotectant described above. As a non-limiting example, a 200 gr 10 mM histidine, 10% sucrose buffer may be prepared. A pH of buffer may be adjusted to approximately 7.2 when measured at 25 degrees Celsius. Buffer may be sterile filtered through a filter such as without limitation a 0.2 µm or 0.22 µm filter. Buffer may then be combined with the antigen mixture; alternatively or additionally, combination with antigen may occur concurrently with or subsequent to reconstitution of lyophilized nanoparticles with buffer. For instance, and without limitation, lyophilized lipid-blend may be hydrated with filtered antigen buffer solution and vortexed and/or sonicated until lipids are hydrated and liposomes are formed. Hydration with antigen solution may form a colloidal vaccine solution. At step 620, colloidal vaccine solution may be extruded, for instance using filtration as described above in reference to FIG. 5, to form desired particle sizes. As a non-limiting example, where positively charged dried lipid-blends as described above, may be hydrated with a specific amount of a corresponding spike protein solution such as without limitation a 40 µg/mL spike protein solution; pH of spike protein solution may match pH of lipid and/or nanoparticle solution. A resulting combined solution may be extruded through filters; for instance, a vaccine particle solution may be extruded through a membrane filter, such as through 2×400 nm membrane filters in an extruder such as a 10 mL extruder. As a further non-limiting example, solution may be extruded ten times through two 400 nm polycarbonate filters in a 10 ml extruder at 50-100 psi using nitrogen gas. Extrusion may be performed gradually, for instance in a laminar flow hood using N2 gas. This procedure may be repeated one or more times; extrusion may be repeated until all solution has passed through the extruder 10 times. A resulting solution may be dispensed in vials; for instance, solution may be dispensed in 3 mL depyrogenated glass vials, for instance filling 800 μL fill volume. Dispensation may be performed in a laminar flow hood. Dispensation may be performed using a fine 1 mL pipette and sterile disposable pipette tips. Preparation according to steps 615 and 620 may be referred to herein as formulation "C"; for instance, where antigen is a solution of S1 spike proteins, formulation may be referred to as CS1, while where antigen is a solution of S1S2 spike proteins, formulation may be referred to as CS1S2.

Alternatively or additionally, and still referring to FIG. 6, at step 625 dried lipid blend may be hydrated with formulation buffer, for instance and without limitation as described above, without antigen to form nanoparticle delivery system alone as a colloidal solution. For instance, and without limitation, lyophilized lipid-blend may be hydrated with filtered buffer, vortexed and/or sonicated until lipids are hydrated and liposomes are formed. Nanoparticle delivery system may be extruded and/or dispensed in vials as described above, as illustrated at step 630.

In some embodiments, and with continued reference to FIG. 6, nanoparticle delivery system as formed at steps 625 and 630 may be combined in its form as a colloidal solution with antigen, for instance by mixing a protein solution of antigen with the colloidal solution of nanoparticles, as illustrated at step 635; this may be implemented, without limitation, as described above in reference to FIG. 5. A formulation as described in reference to steps 625, 630, and 635 is referred to herein as formulation "A"; for instance, where antigen is a solution of S1 spike proteins, formulation may be referred to as AS1, while where antigen is a solution of S1S2 spike proteins, formulation may be referred to as AS1S2.

Alternatively or additionally, and still referring to FIG. 6, nanoparticle delivery system may be lyophilized, as illustrated at step 640. At step 645, lyophilized nanoparticle delivery system may be reconstituted with antigen, for instance and without limitation using antigen in a buffered solution. A formulation as described in reference to steps 625, 640, and 645 is referred to herein as formulation "B"; for instance, where antigen is a solution of S1 spike proteins, formulation may be referred to as BS1, while where antigen is a solution of S1S2 spike proteins, formulation may be referred to as BS1S2. In an embodiment, reconstitution of freeze-dried nanoparticles ("B") with spike protein antigens to be trapped within a vesicle such as an aqueous interior of a liposome, as well as adsorbed to and/or trapped in lipid layer 108, for instance as illustrated above in reference to FIG. 4. In an embodiment, mixture of lyophilized delivery system with antigen may be performed shortly before administration; in other words, lyophilized delivery system and antigen may be transported and/or stored separately and combined at or near a site of administration.

At step 650, and still referring to FIG. 6, any vaccine formulation described above may be lyophilized. Lyophilized vaccines may be denoted as formulation "D"; for instance, where antigen is a solution of S1 spike proteins, formulation may be referred to as DS1, while where antigen is a solution of S1S2 spike proteins, formulation may be referred to as DS1S2. At least one lyoprotectant as described above may be included with combination of antigen with nanoparticle delivery system. Lyophilization and/or inclusion of lyoprotectants may be accomplished in any manner consistent with descriptions provided above. For instance, and without limitation vaccines may be filled in vials and freeze-dried in a freeze-drier such as a Vertis Genesis 12XL by first freezing the solution to −45° C. at 0.5° C./min, followed by a 2-hour hold. Further continuing the example, primary drying may be performed below the primary glass transition of the frozen solution (Tg'), for example at −35° C. shelf temperature for at least 10 hours at a chamber pressure of 100 mTorr or until completion of primary drying. After primary drying, and still continuing the example, a shelf may be ramped up to 25° C. at 0.2° C./min. Still continuing the example, secondary drying may be performed at 25° C. shelf temperature for 4 hours at a chamber pressure of 100 mTorr. Second lyophilization of combined proteins and liposomes may cause a complex interaction between antigen, such as S1 or S1S2, and lipids and/or sugar and/or other lyoprotectant. At step 655, freeze-dried vaccines, such as freeze-dried S1 and S1S2 liposomal vaccines (referred to here as D-S1 and D-S1S2) may be reconstituted with water for injection (WFI). A resulting liposome solution may include a 25 mg/mL liposome (or between 1 and 50 mg/mL) and 10 ug/mL S1 or S1S2. Alternatively, lyophilized vaccine may be directly administered.

At step 660, vaccine may be administered, according to any suitable process for administration, including without limitation any process described in this disclosure. The above-described methods are provided for exemplary purposes only; any combination of method steps as described in this disclosure is considered within the scope of this disclosure.

Reference is now made to immunization study results regarding study of immunization to coronavirus in mice. Study was conducted according to an approved Animal Care and Use Protocol (ACUP). 2×50 μl of each formulation tested was injected intramuscularly (im) in the leg of five female BALB-C mice on days 0 and 14. Serum was collected from the immunized mice as well as naïve mice (negative control; non-vaccine injected) on Days 14 and 28. Five mice were tested per group.

An antibody response to each vaccine was determined using an Indirect Enzyme-Linked Immunosorbent Assay (ELISA) method that was designed for the detection of mouse antibodies against SARS-CoV-2 spike proteins. Each microtiter plate (Coster 3369, EIA/RIA Plate) was coated with 0.1 μg of S1 per well or 0.2 μg of S1/S2 per well; testing indicated that use of 0.1 μg of S1/S2 produced similar results. Sera from mice were diluted 100-fold in blocking buffer (0.5% Bovine albumin serum (BSA) in 0.05% Polysorbate 20-20). The diluted sera were serially diluted in duplicate to a final dilution of 6,400 times the initial sera. The plates were incubated at 5° C. overnight (16-18 hours). After washing the plates, horseradish peroxidase-conjugated Goat anti-mouse IgG secondary Antibody (HRP), Sino Biological) was diluted (1 μL/10 mL) in blocking buffer and 100 ul was added to each well to detect the antibodies against spike protein. After a 1-2-hour incubation at 37° C., the plates were washed and tetramethylbenzidine (TMB) substrate was added to detect Ab responses. The reaction was stopped after approximately 5 minutes with 1 N HCl. Immediately, absorbance was measured at 450 nm using a Spectromax 190 microplate reader (Molecular Devices, Calif.). Endpoint titer for each mouse was determined as the highest dilution of immune serum producing ELISA values ($A_{450}$ nm) greater than or equal to five times the binding detected with a corresponding dilution of naïve mice sera. The mean $A_{450}$ values obtained for the antibodies were calculated for each group of mice per vaccine. In all cases the results are the mean value of IgG titer absorbance for five mice. Samples were stored at 5 C, 25 C, and 40 C up to one month for stability evaluation. Stability was assessed by measurement of particle size and UV absorbance. Freeze-dried vaccine was found to be stable for at least two weeks at 40 degrees C., and one month at 25 degrees; as a result, vaccine may be suitable for transport and storage without refrigeration.

All samples were analyzed on a Precision Detector Dynamic Light Scattering (DLS) instrument PD2000DLS$^{plus}$ and PDDLS/CoolBatch 90T using quartz cuvettes (Precision Detectors). Liposomal samples were diluted 197 times in histidine sucrose buffer, from an original 25 mg/ml suspension. Measurements were done at 20° C. using a refractive index of 1.3479 and a viscosity of 0.0133 Poise for a 10% sucrose solution. Sample time was 15 μsec with a 3 sec run duration and a total of 60 accumulations per measurement. Data was analyzed using Precision Deconvolve software. Stock solutions of S1 and S1S2 (at 250 and 550 μg/mL, respectively) and also 10 μg/mL solutions of S1 and S1S2 were also analyzed without dilution. Particle size was found to be stable between samples.

Referring now to FIG. 7, a bar graph illustrates experimental results comparing IgG immune response (vertical axis) measured from sera extracted from mice vaccinated using embodiments of disclosed vaccine in which the antigen was an S1 protein without S2 protein component. ELISA was performed with S1-immobilized plates. Naïve samples (unvaccinated) were compared to sera samples from mice vaccinated with four other formulations of a solution of S1 glycoproteins, denoted "S1,", a vaccine formulated using a lipid blend that has not be lyophilized, which was mixed with antigens (in this case S1), which process is referred to in the graphs as "A-S1" as described above in reference to FIG. 6, a formulation of lipid blend lyophilized and reconstituted with S1 spike proteins, referred to in the graphs as "B-S1" as described above in reference to FIG. 6, and a formulation of freeze-dried lipid blend reconstituted with spike protein (S1) solution, then freeze-dried again, and reconstituted a second time, denoted formulation "D-S1" as described above in reference to FIG. 6. As shown in FIG. 6, A-S1, B-S1, and D-S1 all formulations significantly outperformed S1 alone and control resulting in a statistically significant increase in S1-neutralizing antibody response, while B-S1 outperformed A-S1 and D-S1 by a significant margin.

Referring now to FIG. 8, a bar graph illustrates experimental results comparing immune response (vertical axis) measured for sera from mice vaccinated using embodiments of disclosed vaccine in which the antigen was an S1 with no S2, placed on plates coated with S1S2. As before naïve control, S1, A-S1, B-S1, and D-S1 solutions were used. As illustrated in FIG. 7, all three vaccines were immunogenic.

Referring now to FIG. 9, a bar graph illustrates experimental results comparing immune response (vertical axis) measured for blood from mice vaccinated using embodiments of disclosed vaccine in which the antigen was an S1S2 vaccine on a plate coated with S1. Formulations included "S1S2," which was a solution of S1S2 alone, "A-S1S2," prepared as described above for A-S1, but with S1S2 spike proteins instead of S1 alone, "B-S1S2," prepared as described above for B-S1, but with S1S2 spike proteins instead of S1 alone, and "D-S1S2," prepared as described above for D-S1, but with S1S2 spike proteins instead of S1 alone. All formulations were significantly more immunogenic than control, with B-S1S2 far outperforming others.

Referring now to FIG. 10, a bar graph illustrates experimental results comparing immune response (vertical axis) measured for blood from mice vaccinated using embodiments of disclosed vaccine in which the antigen was an S1S2 vaccine on a plate coated with S1S2. Formulations included S1S2, A-S1S2, B-S1S2, and D-S1S2. All formulations were significantly more immunogenic than control, with D-S1S2 and A-S1S2 outperforming B-S1S2.

Referring now to FIG. 11, a graph showing experimental results of stability assessments at one month as described above is provided. Formulations C-S1 and C-S1S2 were not lyophilized. Formulations B-S1 and B-S1S2, which have been described above, were reconstituted, with antigens, as described above at a time of stability assessment. Formulations D-S1 and D-S1S2 were reconstituted at a time of assessment as well. As illustrated in FIG. 11 and shown in Table 1 with respect to particle size, Lyophilized vaccines (D-S1 and D-S1S2) and lyophilized delivery system (B) were stable at 25 C for at least 5 weeks, and at 40 C for at least 2 weeks. When lyophilized delivery system B was reconstituted at t0 with S1 protein, it resulted in a vaccine particle with a size that did not change significantly if the delivery system was stored for 5 weeks at 25 or for 2 weeks at 40 C. This would indicate that the liposomal delivery system B is stable at 25 for at least 5 weeks and at 40 C for at least 2 weeks.

Referring now to FIGS. 12 and 13, representative histograms illustrating the effects of temperature on stability of B and D formulations, respectively. Lyophilization increased vaccine stability at 25° C. and 40° C. FIG. 12 illustrates by dynamic light scattering (DLS) experimentation that particle diameter is not significantly altered between vaccine formulation by the addition of different antigens. FIG. 13 illustrates by DLS that particle diameter may not be significantly altered by expended periods of time (1 month) at ambient room temperature (25° C.) or at elevated temperature (40° C.), demonstrating the stability of the nanoparticle formulation outside of the cold chain. Liquid vaccines C-S1 and C-S1S2 were not stable at either temperature for 2 weeks.

TABLE 1

| Vaccine | t0 | 2w 25 C. | 5w, 25 C. | 2w 40 C. | 5w, 40 C. |
|---|---|---|---|---|---|
| B | 176 ± 3 | | | 173 ± 6 | |
| B-S1 | 176 ± 3 | — | 186 ± 6 | 170 ± 2 | 166 ± 3 |
| B-S1S2 | 178 ± 2 | — | — | — | — |
| C-S1 | 193 ± 4 | 225 ± 5 | — | 1,257 ± 266 | — |
| C-S1S2 | 196 ± 3 | 221 ± 3 | — | 326 ± 30 | — |
| D-S1 | 198 ± 4 | — | 203 ± 16 | 326 ± 74 | 262 ± 9 |
| D-S1S2 | 218 ± 7 | | 209 ± 5 | 269 ± 22 | 355 ± 52 |

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments according to this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An immunogenic composition forming a vaccine, the composition comprising:
a nanoparticle delivery system comprising at least a nanoparticle, wherein the at least a nanoparticle comprises a lipid layer exterior including a plurality of lipids, wherein the plurality of lipids comprises dipalmitoyl phosphatidylcholine (DPPC), dioleoylphosphatidylcholine (DOPC), cholesterol, and a primary alkyl amine including a positively charged amino group head and at least a carbon tail and wherein the DPPC: DOPC: cholesterol: alkyl amine molar ratio is 20-40:15-30:20:10-45; and
an antigen incorporated in the at least a nanoparticle, wherein:
the antigen comprises a nucleic acid encoding at least a part of a spike protein,
wherein the spike protein includes a SARS-COV-2 S2 protein; and
the antigen is combined with the nanoparticle delivery system by:
lyophilizing the at least a nanoparticle; and
reconstituting the at least a nanoparticle using a solution containing the antigen.

2. The immunogenic composition of claim 1, wherein the primary alkyl amine includes stearylamine.

3. The immunogenic composition of claim 1, wherein:
the antigen has an electric charge with a first polarity; and
the lipid layer exterior has an electric charge with a second polarity, wherein the first polarity differs from the second polarity.

4. The immunogenic composition of claim 1, wherein the spike protein further includes an S1 protein.

5. The immunogenic composition of claim 1, wherein the spike protein includes an S1S2 protein.

6. The immunogenic composition of claim 1, wherein:
the at least a nanoparticle comprises a liposome; and
the nucleic acid is trapped in an aqueous compartment of the liposome.

7. The immunogenic composition of claim 1, wherein:
the lipid layer further comprises a plurality of layers; and
the nucleic acid is entrapped between layers of the plurality of layers.

8. The immunogenic composition of claim 1, wherein the immunogenic composition is formulated as a lyophilized composition.

9. The immunogenic composition of claim 1, wherein the nanoparticle delivery system is reconstituted with a combination of the antigen with a buffer solution.

10. The immunogenic composition of claim 1, further comprising at least one lyoprotectant.

11. The immunogenic composition of claim 1, wherein the nucleic acid further comprises at least a sequence encoding a glycoprotein.

12. The immunogenic composition of claim 1, wherein the nucleic acid includes at least a sequence of ribonucleic acid (RNA).

13. The immunogenic composition of claim 12, wherein the at least a sequence of RNA comprises at least a sequence of mRNA.

14. The immunogenic composition of claim 1, wherein the lipid layer comprises an electric charge.

15. The immunogenic composition of claim 1, wherein the lipid layer comprises a lipid blend.

16. The immunogenic composition of claim 1, wherein the immunogenic composition is formed by lyophilizing a lipid blend, reconstituting the lyophilized lipid blend with a buffer solution, and adding the antigen to the reconstituted lipid blend.

17. The immunogenic composition of claim 1, wherein the lipid layer exterior includes cholesterol in an amount ranging from 10 mol % to 20 mol %.

18. The immunogenic composition of claim 15, wherein the lipid blend is freeze-dried.

19. The immunogenic composition of claim 15, wherein the lipid blend is powdered.

20. The immunogenic composition of claim 15, wherein the immunogenic composition is formed by lyophilizing the lipid blend and reconstituting the lyophilized lipid blend with the antigen.

21. The immunogenic composition of claim 1, wherein the at least a nanoparticle has a diameter between 1 and 2000 nanometers in diameter.

* * * * *